United States Patent [19]

Wyburn-Mason

[11] 4,183,941
[45] Jan. 15, 1980

[54] TREATMENT OF RHEUMATOID ARTHRITIS AND RELATED DISEASES

[75] Inventor: Roger Wyburn-Mason, Richmond, England

[73] Assignee: John R. A. Simoons, Summit, N.J.

[21] Appl. No.: 935,401

[22] Filed: Aug. 21, 1978

[51] Int. Cl.² ............................................. A61K 31/415
[52] U.S. Cl. ................................ 424/273 R; 424/248.4
[58] Field of Search ........................................... 424/273

[56] References Cited

U.S. PATENT DOCUMENTS 4,073,922  2/1978  Mason ............................... 424/273 R
4,119,723  7/1977  Mason ............................... 424/273 R Primary Examiner—Stanley J. Friedman
Attorney, Agent, or Firm—Richard T. Laughlin

[57] ABSTRACT

It is believed that rheumatoid arthritis and related collagen and auto-immune diseases are an infection and that various species of free-living (limax) amoebae are the aetiological agent of these diseases. It has been discovered that certain nitroimidazole compounds, anti-mycotic drugs with anti-protozoal activity, are effective for the treatment of rheumatoid arthritis and other collagen and auto-immune (rheumatoid) diseases.

6 Claims, No Drawings

TREATMENT OF RHEUMATOID ARTHRITIS AND RELATED DISEASES

BACKGROUND OF THE INVENTION

Men and other animals are continually exposed to infections and re-infection by various species and strains of free-living limax amoebae which can be detected in the faeces, nasopharynx and bronchi. In all parts of the world they form part of the environment. Experimentally in animals they induce changes like those of collagen and auto-immune diseases and are characterized by vasculitis, myositis, hepatitis, pyelitis and splenomegaly. They can often be seen in the tissues of animals. Such animals show lymphadenopathy with the appearance like that of human Hodgkin's disease or a state like that of advanced malignant disease. These organism may also be recovered from all the tissues of cases of collagen and auto-immune diseases and from human and many animal tumors and may also occur in the tissues of apparently healthy individuals. They cannot be identified in ordinary sections, but can be demonstrated by immunofluorescent methods.

The definite cause of rheumatoid arthritis is presently unknown. Rheumatoid arthritis is a crippling disease, characterized by the inflammation of several joints of the body, with swelling, pain and stiffness. Rheumatoid arthritis is a disorder that afflicts about fifteen million people in the Western World alone. Successful early treatment may avert the destructive, deforming phase of the disease. Therapy has been directed largely at non-specific suppression of inflammatory and immunologic processes. Aspirin is the cornerstone of therapy for rheumatoid arthritis and can reduce pain in a majority of patients in view of its analgesic action. Widespread interest in rheumatoid arthritis arose when Hench (1949) introduced cortisone in treatment. Chemical compounds which have been commonly used in treating rheumatoid arthritis are corticosteroids, gold salts, anti-malarial drugs, immunosuppressive agents and a whole range of so-called non-steroidal drugs, e.g. indomethacin, phenylacetic acid (Ibuprofen), propionic acid (Naproxen) and D-Penicillamine. Most of these drugs being temporary relief to the arthritic patient but present the danger of side effects and the physician has to balance the potential benefit against the risks. However, arthritis reoccurs following withdrawal of such chemical treatment. For many years rheumatoid arthritis was considered to be an infection (Hollander et al., 1960; Robinson, 1967), but with the advent of the concept of auto-immunity this idea lost favor. Such a view has recently been revived (Lancet, 1970, 2, 303) and is supported by many observations. It is highly likely that the limax amoebae, found in all the collagen and auto-immune diseases, may well be the aetiological agent of these conditions and that anti-protozoal drugs may help by their action on these organisms.

The use of a bis-phenyl (2-halophenyl)-1-imidazolylmethane (e.g. clotrimazole) for the treatment of rheumatoid arthritis is disclosed in my U.S. Pat. No. 4,073,922 issued on Feb. 14, 1978. The use of tinidazole and related compounds is disclosed in my U.S. patent application Ser. No. 813,922, filed July 8, 1977, now U.S. Pat. No. 4,119,723. It has also been suggested to use a nitroimidazole derivative in the treatment of rheumatoid arthritis in the Journal of Tropical Medicine and Hygiene v. 75, p. 64 to 66, Mar. 1972.

Various other anti-protozoal drugs were tried on cases of rheumatoid diseases or of various localized manifestations of this. The substances investigated were 4-aminoquinolines (chloroquine), hydroxychloroquine (plaquenil), amodiaquine (camoquin), copper sulfate and bile salts (dehydrocholine), which are effective in killing the trophozooites of many amoebae in the concentration found in the small intestine. All of these were actually shown experimentally to kill amoebae. In addition, other anti-protozoal drugs were also investigated. They include suramin, pentamidine, dehydroemetine (DHE or mebadin), metronidazole (flagyl), nimorazole (naxogin), phanquone (entobex) and diloxanide (furamide).

The 4-aminoquinolines have been given orally in a dose of 200 and 400 mg. daily, reduced after a month to 200 mg. twice weekly, care being given to examine the eyes at intervals to guard against keratitis or macular changes. Copper salts were administered as 25 mg. of copper sulfate in aqua chloroformi by mouth three times daily. This may produce vomiting and/or diarrhea and the dose has to be decreased to 10 mg. three times daily. Only a small amount of the metal is absorbed, however, and no other side effects are observed even when taken over several months. Bile salts as dehydrocholine were given in a dose of 500–1000 mg. three times a day by mouth. They may produce mild colic. Pentamidine was at first given by intramuscular injection into the buttock in doses of 200 mg. daily for ten days. The course was repeated twice with intervals of seven days between. This substance is liable to produce local necrosis or abscess formation. Pentamidine can be given by mouth, but the absorption is uncertain. Capsules containing 200 mg. were especially made and a dose of 200 mg. twice daily to 400 mg. three times daily by mouth were tried in various combinations. Suramin was given by intravenous injection of 500 mg. in 10 ml. of water and after this every four hours 1 g. was injected until 10 g. had been given. The course was repeated once after four months. Dehydro-emetine (DHE) was given by intramuscular injection in doses of 60 mg. daily for ten days and repeated after seven days, or 60 mg. three times daily by mouth for 7–10 days, repeated after an interval of ten days. Before commencing treatment E.C.G.'s were taken and repeated before each successive injection. Metronidazole (flagyl) was given in doses of 400 to 600 mg. three times daily by mouth and nimorazole (naxogin) in doses of 75 mg. three times daily. Phanquone (entobex) was given in doses of 100 mg. twice daily by mouth for seven days, repeated at intervals of a week, Diloxanide (furamide) was given in doses of 500 mg. three times daily for ten days and repeated once.

The various substances tested above were tried on cases of rheumatoid arthritis of varying severity, systemic lupus erhthematosus, dermatomyositis and other manifestations of collagen and auto-immune disease and observations made on the clinical condition, oedema, morning stiffness, E.S.R., plasma proteins, RF, ANF and organ-specific antibodies in the serum. No attempt at a double-blind trial was made as its became obvious, fairly early or even the day after commencing treatment, whether beneficial results were obtained and furthermore, symptomatic improvement is associated with improvement or disappearance of the abnormal blood changes, indicating that the drug was effective and improvement not due to suggestion. No beneficial effect was obtained from flagyl, naxogin, entobex, suramine or furamide in the doses used. However, Abd-Rabbo et al. (1972), using a derivative of nitro-imidazole BT 985 Merck A.G., which is active against amoebae, giardia and trichomonas, obtained beneficial effects in one case of systemic lupus erythematosus and nine of ten cases of rheumatoid disease. The drug was given in doses of 250 mg. daily for 14–39 days. In the follow up period of 3–6 months no treatment was given and it was noted that the pain recurred, yet not to the same degree as before the treatment.

It has now been discovered that certain substituted imidazole compounds which have anti-protozoal activity are effective for treating rheumatoid arthritis and related collagen and auto-immune (rheumatoid) diseases.

The method of determining the anti-protozoal activity of drugs on limax amoebae was described by Fulton, C. Methods in Cell Biology (edited by D. M. Prescott), p. 341, New York, 1070, and followed by Jamieson and Anderson in Lancet, 1974, 1, 261. All experiments were performed using 5-day old 5 ml. cultures of amoebae in the axenic medium "A" of Fulton. A standard inoculum of 100 c.mm. of differing concentrations of amoebae was added to each 1 ml. tube containing the dilutions of the compound to be tested (dissolved initially in dimethyl sulfoxide) or other drugs in the axenic medium. The tubes were incubated for 5 days at 37° C. and the final concentrations per c.mm. was compared with the initial count to determine percentage kill.

The effective compounds have the general formula:

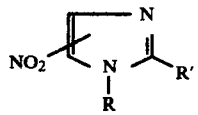

wherein the nitro group is in the 4 or 5 position, R' is hydrogen, lower alkyl of from 1 to 7 carbon atoms, or a halogen such as fluoro, iodo, chloro or bromo, and R is

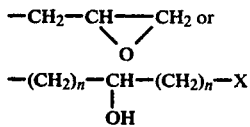

wherein n is a whole integer from 1 to 4 and may be the same or a different number and x is halogen as described above, or

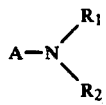

wherein A is alkylene of 1 to 6 carbon atoms and $R_1$ and $R_2$ are ethyl or when taken together, along the N-atom are morpholine or pyrrolidino. In these latter compounds a halogen can be in the position not occupied by the nitro group and the pharmaceutically acceptable acid addition salts thereof. Particularly useful compounds are when the nitro group is in the 5-position, R' is hydrogen or methyl and R is either

or

CH$_2$—CH(OH)—CH$_2$—X wherein A and X are as defined above. The preparation of these compounds are described in U.S. Pat. No. 3,435,049 issued Mar. 25, 1969 to Max Holler or U.S. Pat. No. 3,399,193 issued Aug. 27, 1968 to Giraldi and Mariotti. In these patents the compounds are described as having activity for treating of infections due to pathogenic protozoa such as trichomonacides. Typical examples of suitable compounds for this invention are the following:

N-β-diethyl-amino-ethyl-5-nitro-imidazole
N-β-diethyl-amino-ethyl-4-nitro-imidazole
N-β-morpholino-ethyl-5-nitro-imidazole (nimorazole)
N-β-morpholino-ethyl-4-nitro-imidazole
N-β-pyrrolidino-ethyl-5-nitro-imidazole
N-β-pyrrolidino-ethyl-4-nitro-imidazole
1-(2,3-epoxypropyl)-4-iodo-2-methyl-5-nitro-imidazole
1-(3-chloro-2-hydroxypropyl)-2-methyl-5-nitro-imidazole (ornidazole)
1-(3-chloro-2-hydroxypropyl)-2-methyl-4-nitro-imidazole
1-(2,3-epoxypropyl)-2-methyl-4-nitro-5-iodo-imidazole
1-(2,3-epoxypropyl)-2-methyl-5-nitro-imidazole
1-(2,3-epoxypropyl)-2-methyl-nitro-imidazole
4-iodo-2-methyl-5-nitro-imidazole
5-iodo-2-methyl-4-nitro-imidazole
1-(3-chloro-2-hydroxypropyl)-5-iodo-2-methyl-4-nitro-imidazole
1-(3-chloro-2-hydroxypropyl)-4-iodo-2-methyl-5-nitro-imidazole
1-(3-chloro-2-hydroxypropyl)-2-iodo-4-nitro-imidazole The salts of the compounds of the invention are the pharmaceutically acceptable non-toxic acid addition salts. Examples of suitable acids are the hydrohalic acids (hydrochloric being preferred), phosphoric acid, mono- and bifunctional carboxylic acids, such as acetic acid, propionic acid, maleic acid, succinic acid, fumaric acid, tartaric acid, citric acid, salicyclic acid, sorbic acid, lactic acid and 1,5-naphthalene-disulphonic acid. The hydrohalides, especially the hydrochlorides, lactates and salicylates are of particular value.

The diagnosis of active rheumatoid arthritis in cases treated was consistent with the criteria of the American Rheumatism Association. The patients were not hospitalized or confined to bed. The drugs they were being treated with when first seen were discontinued. Serial investigations were carried out before and repeated during and after treatment. Nimorazole (Naxogin) and Ornidazole (Tiberal) have a marked effect in abolishing the symptoms and signs of active rheumatoid disease and have been used so far in 35 cases. In cases of trichomonas infection or amoebiasis these drugs produced no generalized disturbance. Their action in this disease is generally to cause within a few hours influenzal-like symptoms often with headache and sweating and generalized aching and an exacerbation of the pain, heat and swelling of the joints affected by active disease and in addition they may cause the appearance of inflammatory changes in previously unaffected joints or in non-articular tissues. These symptoms may be accompanied by a mild pyrexia and by sweating and last two to three days. This response constitutes an herxheimer reaction and suggests the drug was destroying an organism sensitive to the drug. This occurs in about two-thirds of treated cases. In the other one-third there occurs no exaggeration of symptoms. The treatment was begun with two 500 mgm. tablets and three days later by a dose of four 500 mgm. tablets taken in one dose. If there is no response to the treatment, this treatment is repeated at weekly intervals. Sometimes a reaction does not occur until several doses have been taken. If there is a reaction then the dosage is not repeated until the reaction has died down. If the first administration produces a reaction, then after subsequent administration the general rule is a gradual diminution in this response until it finally disappears at which time treatment semi-monthly. There is a gradual disappearance of signs and symptoms of inflammatory activity in the affected joints. Anaemia and raised ESR if present at the beginning is not seen until about four weeks after cessation of treatment. Cases have now been followed for up to a year without evidence of recurrence of active disease. Bony cartilaginous changes are, of course, not reversible but this form of treatment halts the progress of the condition and in early cases all signs and symptoms of the disease disappear.

The therapeutically effective compound can be used either as such or in combination with pharmaceutically acceptable carriers. Suitable forms of administration in combination with various inert carriers are tablets, capsules, powders, aqueous suspensions, syrups and the like. In the aforesaid case, the therapeutically active compound should be present in the total mixture at a concentration of about 0.5 to 90.0 percent by weight, i.e., in quantities which suffice to attain the range of dosage mentioned above. Tablets may also contain fillers such as starch, avicel, lactose, or dicalcium phosphate together with various additives such as dyes and binders. Typical of such materials are polyvinylpyrrolidine, methyl cellulose, gelatin and the like. It is further required to add lubricants such as magnesium stearate, stearic acid or talc for producing tablets. Tablets can also be film coated.

A typical example for making a tablet is as follows:

EXAMPLE A

|  | Weight |
| --- | --- |
| Micronized imidazole compound | 0.75 Kg. |
| Cornstarch powder | 0.08 Kg. |
| Avicel (microcrystalline cellulose) PH 102 | 0.27 Kg. |
| Methocel 50 HG, 60 CPS | 15.00 gm. |
| Purified water | q.s. |

The imidazole compound is mixed in a suitable blender with the other components and then granulated mass is passed through an oscillator equipped with a 20-mesh screen. The granules are dried in an air circulating oven at 50° C. until a moisture content of less than 3% is reached. The granules are screened through a 20-mesh screen, lubricated with steric acid and mg. of magnesium stearate. The final mix is compressed into tablets of 750 mg. each, which contain 500 mg. of the imidazole compound per tablet and can be used for oral administration.

Any departure from the foregoing description conforms to the present invention is intended to be included within the scope of the claims.

What is claimed is:

1. A method for producing remission in patients suffering from active rheumatoid arthritis which comprises administering to such a patient an effective amount to produce such remission of a compound of the formula:

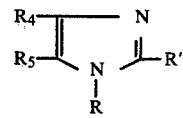

wherein R' is hydrogen, lower alkyl or a halogen, R is

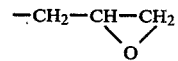

or $-(CH_2)_n-CH(OH)-(CH_2)_n-X$ wherein n is a whole integer from 1 to 4 and may be the same or different, X is a halogen, and one of $R_4$ and $R_5$ is $NO_2$, and the pharmaceutically cceptable acid addition salts thereof.

2. The method of claim 1 wherein in said compound R' is methyl, $NO_2$ is in the 5-position, R is $-(CH_2)_n-(CH(OH)-(CH_2)_n$ n is a whole integer from 1 to 4 and may be the same or different and X is a halogen 3. The method according to claim 2, wherein the compound is 1-(3-chloro-2-hydroxypropyl)-2-methyl-5-nitro-imidazole.

4. The method of claim 3, wherein said compound is administered orally in doses of approximately 20 to 50 mg. per kilogram of body weight daily, every other day or once weekly.

5. The method of claim 4, wherein the compound is administered orally in a weekly dose amount of about 1.0 g. to about 3.0 g.

6. The method of claim 2, wherein the compound is administered orally in doses of approximately 20 to 50 mg. per kilogram of bodr weight daily, every other day or once weekly.

* * * * *